(12) United States Patent
Mäntylä et al.

(10) Patent No.: US 11,828,736 B2
(45) Date of Patent: Nov. 28, 2023

(54) MEASUREMENT OF ELASTIC MODULUS OF MOVING WEB

(71) Applicant: Valmet Automation Oy, Espoo (FI)

(72) Inventors: Markku Mäntylä, Espoo (FI); Jussi Graeffe, Espoo (FI); Anna-Leena Erkkilä, Jyväskylä (FI)

(73) Assignee: Valmet Automation Oy, Espoo (FI)

( * ) Notice: Subject to any disclaimer, the term of this patent is extended or adjusted under 35 U.S.C. 154(b) by 554 days.

(21) Appl. No.: 17/052,537

(22) PCT Filed: Apr. 24, 2019

(86) PCT No.: PCT/FI2019/050327
§ 371 (c)(1),
(2) Date: Nov. 3, 2020

(87) PCT Pub. No.: WO2019/211515
PCT Pub. Date: Nov. 7, 2019

(65) Prior Publication Data
US 2021/0239583 A1   Aug. 5, 2021

(30) Foreign Application Priority Data
May 3, 2018 (FI) .................................. 20185410

(51) Int. Cl.
*G01N 3/20* (2006.01)
*B65H 23/04* (2006.01)
(Continued)

(52) U.S. Cl.
CPC ............. *G01N 3/20* (2013.01); *B65H 23/044* (2013.01); *D21F 1/48* (2013.01); *D21G 9/0027* (2013.01);
(Continued)

(58) Field of Classification Search
CPC ................... G01N 3/20; G01N 33/346; G01N 2203/0046; G01N 2203/0075;
(Continued)

(56) References Cited

U.S. PATENT DOCUMENTS 3,677,076 A  7/1972 Herzhoff et al.
3,718,037 A  2/1973 Stringer et al.
(Continued)

FOREIGN PATENT DOCUMENTS

EP  0253644 A2 *  1/1988  ........... G01N 33/346
EP  1273879 A2  1/2003
(Continued)

*Primary Examiner* — Michael A Lyons
(74) *Attorney, Agent, or Firm* — Laine IP Oy

(57) ABSTRACT

According to an example aspect of the present invention, there is provided a method, comprising: controlling suction with predetermined force in a known measurement area to a moving cardboard or paper web in a manufacturing process, detecting on-line measurement information on deviation of the moving cardboard or paper web in the manufacturing process caused by the suction with predetermined force in the known measurement area, and determining elastic modulus of the moving cardboard or paper web in the manufacturing process on the basis of the measured deviation.

14 Claims, 5 Drawing Sheets

(51) Int. Cl.
*D21F 1/48* (2006.01)
*D21G 9/00* (2006.01)
*G01B 11/16* (2006.01)
*G01N 33/34* (2006.01)
*G01B 11/06* (2006.01)

(52) U.S. Cl.
CPC ........... *G01B 11/06* (2013.01); *G01N 33/346* (2013.01); *B65H 2511/23* (2013.01); *B65H 2515/37* (2013.01); *B65H 2553/10* (2013.01); *B65H 2553/45* (2013.01); *G01N 2203/0046* (2013.01); *G01N 2203/0075* (2013.01); *G01N 2203/0282* (2013.01)

(58) Field of Classification Search
CPC .. G01N 2203/0282; G01N 3/10; G01B 11/16; B65H 23/044; B65H 2515/37
USPC .................................................. 356/429–431
See application file for complete search history.

(56) References Cited

U.S. PATENT DOCUMENTS

| | | | |
|---|---|---|---|
| 4,866,984 A | 9/1989 | Houghton | |
| 5,029,469 A | 7/1991 | Chase et al. | |
| 2003/0024301 A1* | 2/2003 | Graeffe | G01B 11/0691 356/402 |
| 2003/0066200 A1* | 4/2003 | Hellstrom | G01N 33/346 33/501.02 |
| 2003/0075293 A1 | 4/2003 | Moeller et al. | |
| 2005/0166670 A1 | 8/2005 | Franz et al. | |
| 2009/0059232 A1 | 3/2009 | Hellström et al. | |
| 2009/0260772 A1 | 10/2009 | Alev et al. | |
| 2010/0078140 A1 | 4/2010 | Hughes | |
| 2013/0116812 A1 | 5/2013 | Drasek et al. | |
| 2015/0097070 A1 | 4/2015 | Duan | |
| 2016/0122946 A1* | 5/2016 | Mäntylä | B05C 11/1015 118/712 |
| 2021/0088500 A1* | 3/2021 | Mäntylä | G01N 21/49 |

FOREIGN PATENT DOCUMENTS

| | | |
|---|---|---|
| JP | 2017173088 A | 9/2017 |
| WO | WO2009010343 A1 | 1/2009 |
| WO | WO2011062106 A1 | 5/2011 |
| WO | WO2013007864 A1 | 1/2013 |
| WO | WO2013116299 A1 | 8/2013 |
| WO | WO2014191626 A1 | 12/2014 |

* cited by examiner

MEASUREMENT OF ELASTIC MODULUS OF MOVING WEB

FIELD

The invention relates to on-line measurement of moving cardboard or paper web, and in particular to measurement of elastic modulus of a moving cardboard or paper web.

BACKGROUND

Elastic modulus indicates an object's or substance's resistance to being deformed elastically when a stress is applied. The elastic modulus of an object is defined as the slope of its stress-strain curve in the elastic deformation region. In the elastic deformation region deformation is non-permanent. A stiffer material will have higher deformation resistance and a higher elastic modulus.

Especially packing cardboard used in cardboard boxes should have sufficient stiffness to keep shape of the boxes in storage and transport. Limiting factor is usually cross direction (CD) stiffness of the cardboard. For example, mass per unit area, thickness, bulk density, mass, processing methods, raw materials, drying environment, CD shrinkage and moisture of cardboard or paper have an effect on stiffness of the cardboard or paper.

The raw material's share of manufacturing costs of the cardboard is usually about 60-70%. When strength and elastic properties depend heavily on the amount of the raw material, treatments and additives used, there is need for measurement of elastic modulus for facilitating optimization of cardboard production costs.

U.S. Pat. No. 718,037 discloses a device for measuring elastic modulus of web comprising a vacuum chamber into which a portion of the width of the web is drawn and the deflection of the web into the chamber measured to provide a measurement of the tension.

SUMMARY OF THE INVENTION

The invention is defined by the features of the independent claims. Some specific embodiments are defined in the dependent claims.

According to a first aspect of the present invention, there is provided an apparatus, comprising: means for controlling suction with predetermined force in a known measurement area to a moving cardboard or paper web in a manufacturing process, means for detecting on-line measurement information on deviation of the moving cardboard or paper web in the manufacturing process caused by the suction with predetermined force in the known measurement area, wherein the means (810) for on-line measurement of deviation comprise a multi-dimensional scanner to define multi-dimensional profile of the cardboard or paper web (20) in the measurement area (500), and means for determining elastic modulus of the moving cardboard or paper web in the manufacturing process on the basis of the measured deviation.

According to a second aspect of the present invention, there is provided a method, comprising: controlling suction with predetermined force in a known measurement area to a moving cardboard or paper web in a manufacturing process, detecting on-line measurement information on deviation of the moving cardboard or paper web in the manufacturing process caused by the suction with predetermined force in the known measurement area, wherein a multi-dimensional profile of the cardboard or paper web (20) in the measurement area (500) is defined by a multi-dimensional scanner, and determining elastic modulus of the moving cardboard or paper web in the manufacturing process on the basis of the measured deviation.

According to a third aspect, there is provided an apparatus comprising at least one processing core, at least one memory including computer program code, the at least one memory and the computer program code being configured to, with the at least one processing core, cause the apparatus at least to carry out the method or an embodiment of the method.

According to a fourth aspect, there is provided a computer program product, a computer readable medium, or a non-transitory computer readable medium comprising program instructions for causing an apparatus to at least perform: control suction with predetermined force in a known measurement area to a moving cardboard or paper web in a manufacturing process, detect on-line measurement information on deviation of the moving cardboard or paper web in the manufacturing process caused by the suction with predetermined force in the known measurement area, wherein a multi-dimensional profile of the cardboard or paper web (20) in the measurement area (500) is defined by a multi-dimensional scanner, and determine elastic modulus of the moving cardboard or paper web in the manufacturing process on the basis of the measured deviation.

EMBODIMENTS

In the present context, the term "cardboard" comprises cartonboards such as folding boxboards, liquid packaging boards, and bleached pulp boards and containerboards consisting of lining and fluting layers. The term "web" refers to cardboard and paper web.

In the present context, the term "cross direction" (CD) refers to direction, which is perpendicular to moving direction of cardboard or paper web in manufacturing process. The term "machine direction" (MD) refers to moving direction of cardboard or paper web in manufacturing process.

Figure 1:
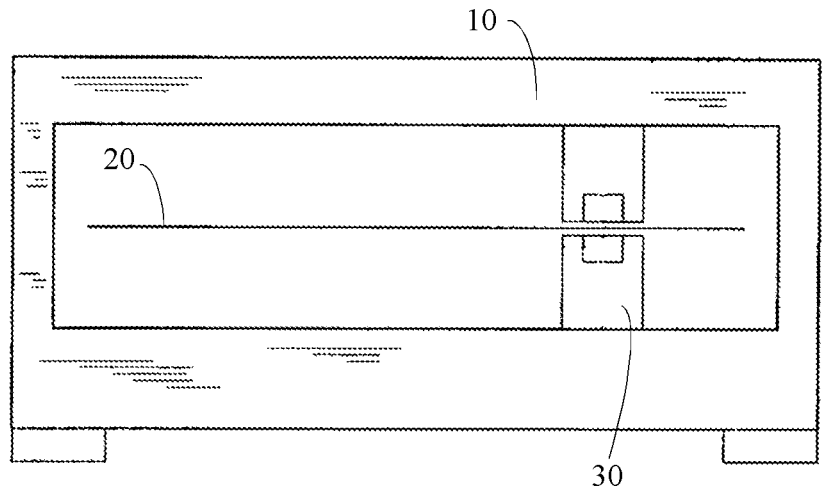
FIG. 1 illustrates an overall measurement environment showing a moving web and a frame for a measurement device.

FIG. 1 illustrates an example measurement environment for on-line measurement of a moving cardboard or paper web 20 and a frame 10 for a measurement device or apparatus configured to measure elastic modulus of moving cardboard or paper web 20 in a cardboard or paper manufacturing process. The measurement apparatus comprise at least one measurement unit 30 configured at least for elastic modulus measurement.

Figure 2:
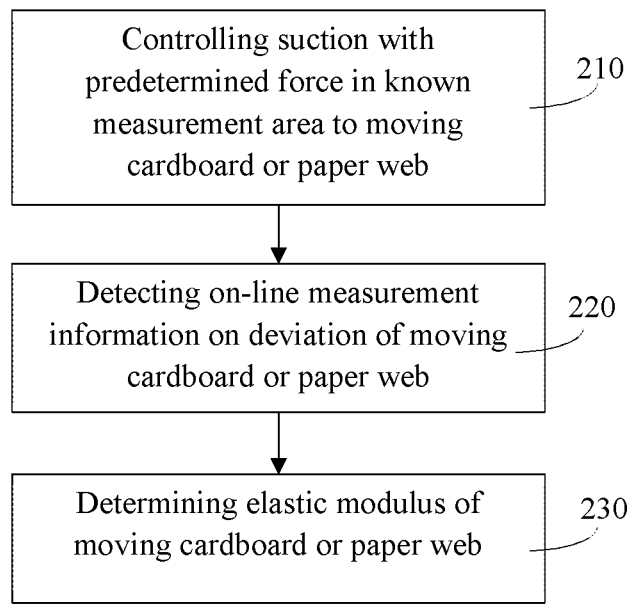
FIG. 2 illustrates method for measuring elastic modulus of a moving cardboard or paper web.

FIG. 2 illustrates a method for measuring elastic modulus of a moving cardboard or paper web. The method may be applied in an apparatus or system configured to at least measure the elastic modulus, such as the measurement unit 30 or a further controller or computing unit thereof. Suction with predetermined force is controlled 210 in a known measurement area 500 to a moving cardboard or paper web 20 in a manufacturing process. On-line measurement information on deviation of the moving cardboard or paper web 20 caused by the suction with predetermined force in the known measurement area 500 is detected 220. The deviation may be measured 220 on-line in the manufacturing process and received by the apparatus performing the method in block 220. Finally, elastic modulus of the moving cardboard or paper web 20 is determined 230 in the manufacturing process on the basis of the measured deviation. Elastic modulus may be calculated in block 230 on the basis of the measured deviation and the known predetermined force.

An apparatus for on-line measurement of elastic modulus of a moving cardboard or paper web may comprise a suction unit for applying the suction with predetermined force to the web 20 in the manufacturing process on the known measurement area 500, a deviation sensing unit for the on-line measurement of deviation of the web 20, and a computing unit for determining 230 the elastic modulus on the basis of measured deviation.

Figure 3:
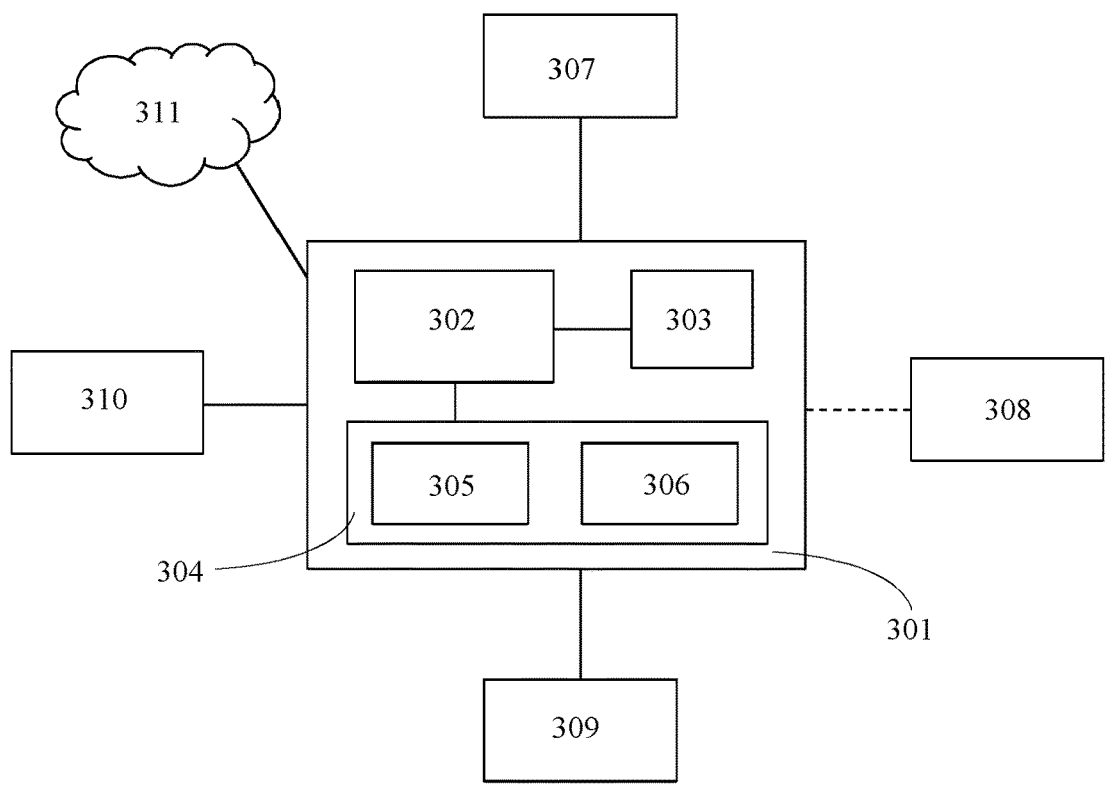
FIG. 3 illustrates a schematic diagram of the elastic modulus measuring system according to one embodiment.

An electronic device comprising electronic circuitry may be an apparatus for realizing at least some embodiments. FIG. 3 illustrates a schematic diagram of an elastic modulus measurement system or apparatus according to an embodiment. The elastic modulus measuring system may be applied at least for cardboard and paper machines. The elastic modulus measuring system may comprise a computing unit 301, a deviation sensing unit 307, a suction unit 308, and a user interface (UI) 309. The system may comprise or be connected to further process automation control unit(s) 310 and network(s)/service(s) 311, such as a cloud service. It is to be appreciated that FIG. 3 illustrates only one example of an applicable elastic modulus measuring system.

The calculation of elastic modulus may be arranged in the computing unit 301 arranged in connection or in the same unit with the deviation sensing unit 307 or in another unit, such as a process automation control 310 and/or monitoring unit, which may be remote from the web measurement in the manufacturing process.

The computing unit 301 may comprise a processor 302, a communications unit 303 and a memory 304. The communication unit 303 may comprise a transmitter and/or receiver, which may be configured to operate in accordance with global system for mobile communication, GSM, wideband code division multiple access, WCDMA, long term evolution, LTE, 5G or other cellular communications systems, wireless local area network, WLAN, and/or Ethernet standards, for example. The computing unit 301 may comprise a short range communication, SRC, transceiver, such as a Bluetooth or Bluetooth Low Energy transceiver.

The memory 304 may store computer program code 305 and parameters 306 for causing the computing unit to perform at least some of the presently disclosed features, such as determining the elastic modulus, when the computer program code is executed by the processor. The memory, processor and computer program code may thus be the means to cause the computing unit 301 to perform at least some of the presently disclosed features related to measuring elastic modulus, such as control in block 210 unit 308, control the unit 307 to measure the deviation, detect 220 the measurement information from the unit 307, and determine 230 the elastic modulus.

The deviation sensing unit 307 provides at least a measurement result of the depth of the deviation (caused by the suction). The deviation sensing unit 307 may be arranged in connection/in same unit with the computing unit 301. In some embodiments, measurement area and/or shape of the deviation may be sensed in connection with block 220 and by the deviation sensing unit. The deviation measurement results are used for determining 230 the elastic modulus.

In some embodiments, the deviation is measured by an optical measurement device, which may be an optical scanner. The optical scanner may be, for example, a lateral chromatic aberration measurement device or a laser scanner.

A lateral chromatic aberration measurement device uses a light source that passes through a series of lenses, which have a high degree of chromatic aberration. The refractive index of the lenses will vary the focal distance of each wavelength of the light. When a measured surface is within the measurement range a single wavelength of the light will be in focus while all others will be out of focus. The light is then reflected back through the lenses, then through a pin hole filter that allows only the focused wavelength to pass through to a spectrometer. It will indicate the wavelength in focus, which corresponds to a specific distance for a single point.

The apparatus may comprise one-dimensional scanner to define the deviation of the web in the measurement area at multiple measurement points, and the means for determining elastic modulus is configured to calculate the elastic modulus of the moving cardboard or paper web on the basis of predefined measurement area dimensions. The one-dimensional scanner may be for example, a laser scanner, such as one-dimensional laser scanner. The one-dimensional laser scanner may define dimension from the plane of the web outside the measurement area to the central point of the deviation of the web. Then, elastic modulus may be calculated on the basis of the defined dimension and the predefined measurement area dimensions.

According to some embodiments, the apparatus comprises a multi-dimensional scanner to define multi-dimensional profile of the cardboard or paper web 20 in the measurement area. The profile may be defined by two or more measurement points or by line measurement. The scanner may be configured to measure distance to the deviated surface of the web and may form a two-dimensional (2D) or three-dimensional (3D) profile of the surface and show deviations across a plane of the web when viewed perpendicularly. A 3D surface scanner may be configured to provide a 3D surface profile of the deviations of the web at least within the measurement area. The 3D scanner may store a set of coordinate points of the examined portion of the web surface, thus forming a point cloud. Based on the analysis of the points, a surface pattern can be produced.

According to some embodiments, at least the deviation sensing unit 306 is provided in a measurement unit, such as the unit 30, arranged to move in cross direction to the movement of the cardboard or paper web 10. This enables to use several measurements points and better measurement accuracy, because the composition of the web may vary along the cross direction of the web.

The suction unit 308 is provided to apply the predetermined force by air suction. For example, the apparatus may comprise a vacuum pump or an ejector air pump. The suction is a non-destructive method for providing a deviation. Mechanical measuring force may damage or even break the web 20, but this can be avoided by applying the predetermined force by air suction. Suction levels in the area of 0-50 kPa have been tested. Also higher suctions levels, even up to 100 kPa may be applicable. In some embodiments, the suction level is in the range of 0-20 or 1-10 kPa.

The suction unit 308 may be placed under the web 20 and the known measurement area 500. It may be arranged in connection or in same unit with the deviation sensing unit 307. The suction unit may be movable according to the cross direction of the web. This enables of using several measurements points and better measurement accuracy, because the composition of the web may vary along the cross direction of the web.

According to one embodiment, a set of selectable suction levels may be applied for applying 210 the suction. The suction may be constant or pulsed. This enables of selecting of suction level according to properties of measured web material.

The UI 309 may comprise one or more user interface devices, such as a display and input means, such as one or more of a keyboard, a touch screen, a mouse, a gesture input device or other type input/output device. The UI may be configured to display the analyzing results and provide user input for controlling the computing unit 301, e.g. to set parameters affecting one or more of operations illustrated in connection with FIG. 2. It will be appreciated that various other data related to the process may be displayed and/or controlled via the UI 309, such as web speed, trends, reports, alarms, etc.

According to an embodiment, the means for determining 230 the elastic modulus, such as the computing unit 301, is configured to convert the measured profile into frequency domain representation. A value indicative of the elastic modulus may then be calculated on the basis of the frequency domain representation of the profile.

The computing unit 301 may comprise for example, a mathematical model, a formula library and an artificial intelligence (AI) module. A measured curve can be fitted with the curves measured and proved in a laboratory and saved in the formula library. While using AI, it can be initially taught on the basis laboratory measurements what kind of curve has certain elastic modulus, and the AI module may be configured to learn and further adjust determination of the elastic modulus on the basis of the measurement data during on-line measurement operations.

According to an embodiment, the apparatus comprises means for determining a value indicative of strain of the moving cardboard or paper web 20 in the direction of movement of the web 40, and the means for determining elastic modulus is configured to calculate the elastic modulus by applying the determined value indicative of the strain. Tightness of the moving web may vary during the manufacturing process and at different production stages. In addition, it has effect on the degree of the deviation. Thus, the elastic modulus measurement accuracy may be further improved.

In some embodiments, the elastic modulus calculation is based on the equation for small transverse displacements. However, it is to be appreciated that the following embodiments illustrate only some examples of determining the elastic modulus and other methods may be applied.

If the orthotropic plate (web), deflected using force q, is moving in the direction x, the equation for small transverse displacements w=w(x,y), can be written in the following form (reference is made to citations [1] and [2]):

$$D_x \frac{\partial^4 w}{\partial x^4} + 2D_{xy} \frac{\partial^4 w}{\partial x^2 \partial y^2} + D_y \frac{\partial^4 w}{\partial y^4} - \qquad (1)$$

$$T_{xx} \frac{\partial^2 w}{\partial x^2} - T_{xy} \frac{\partial^2 w}{\partial x^2 \partial y^2} - T_{yy} \frac{\partial^2 w}{\partial y^2} + mV^2 \frac{\partial^2 w}{\partial x^2} = q(x, y),$$

where x and y are the in-plane directions corresponding machine and cross direction (MD and CD) of paper or board web, respectively, q is the transverse load [N/m$^2$], the m is the mass of the web per unit area and V is the axial velocity of the web in the direction x (MD).

$T_{xx}$, $T_{xy}$ and $T_{yy}$ are in-plane tensions (force per unit length) and related corresponding stress tensor components $\sigma_{ij}$ by the expressions $T_{ij}=h\sigma_{ij}$, where the h is the thickness of the web. $D_x$, $D_{xy}$ and $D_y$ are the bending rigidities. In the case of plate, the following expressions can be written:

$$D_x = \frac{h^3}{12} C_{11}, \qquad (2)$$

$$D_{xy} = \frac{h^3}{12}(C_{12} + C_{66}),$$

$$D_y = \frac{h^3}{12} C_{22}$$

where $C_{ij}$ are the elastic moduli. Further $$C_{11} = \frac{E_1}{1 - v_{12}v_{21}}, \qquad (3)$$

$$C_{22} = \frac{E_2}{1 - v_{12}v_{21}},$$

$$C_{12} = \frac{v_{21}E_1}{1 - v_{12}v_{21}}, \qquad (4)$$

$$C_{66} = G_{12} \approx \frac{\sqrt{E_1 E_2}}{2(1 + \sqrt{v_{12}v_{21}})}.$$

where $E_1$ and $E_2$ are Young's moduli in the x (MD) and y (CD) directions, $G_{12}$ is the shear modulus in xy plane, and $v_{12}$ and $v_{21}$ are Poisson ratios in the xy plane.

When considering the variables in equation (1), it can be assumed that m and V are known, q may be measured or known at least in the middle of studied region, and w is measured from different xy positions either as 2D-line profiles or as 3D topography map. Derivatives of w can be determined numerical differentiation, reference is also made to [3] or [4]. Six unknown variables remain i.e. $D_x$, $D_{xy}$, $D_y$, $T_{xx}$, $T_{xy}$, and $T_{yy}$, which can be determined from system of six or more linear equations as an overdetermined system. Equations for linear system can be produced by varying the pressure.

To simplify the analysing procedure, the determination can be first made for oblong opening (length to width ratio at least 4:1) with the long edge of the hole along the CD. In that case, it can be expected that the derivatives of transverse displacements are very small in CD. Then, the MD tension, MD bending rigidity and centripetal acceleration are the only significant terms in the equation (1) i.e. the equation (1) can be reduced:

$$D_x \frac{\partial^4 w}{\partial x^4} - T_{xx} \frac{\partial^2 w}{\partial x^2} + mV^2 \frac{\partial^2 w}{\partial x^2} = q, \quad (5)$$

When equation (5) can be applied, measurements at least with two pressure levels is minimum for solving the linear system. Now, the dominating parameters $D_x$ and $T_{xx}$ are determined and can be insert the general equation (1). Using this partly solved equation (1), the rest of the unknown variables can be solved using shape of hole, which is more favourable for determining of CD stiffness $D_y$.

By using equation on the compatibility relation $$v_{21}E_1 = v_{12}E_2$$

and equations (2), (3) and (4), the Young's modulus, Poisson ratios and shear modulus can be determined.

Figure 4:
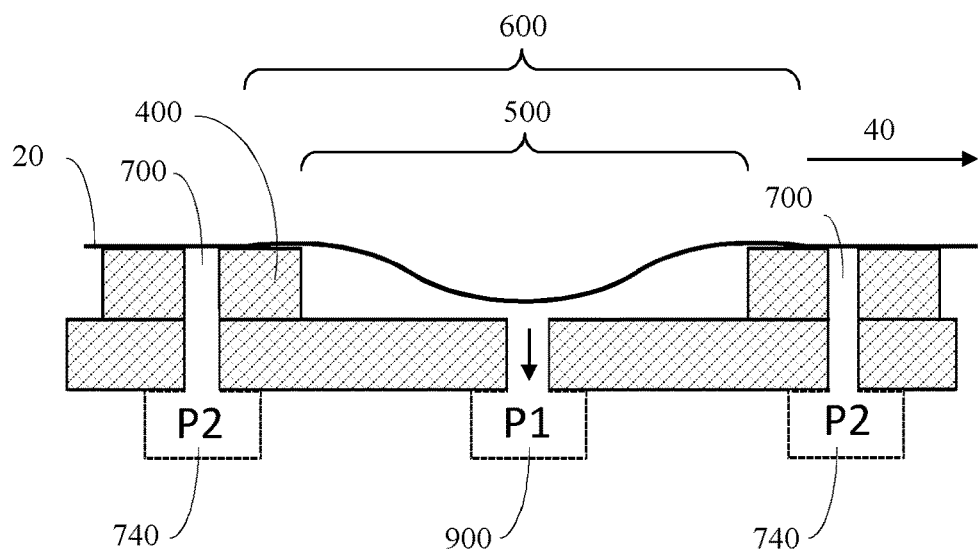
FIG. 4 illustrates a cross section view of a measurement arrangement according to one embodiment.

FIG. 4 illustrates a cross section view of a measurement arrangement according to an embodiment. The known measurement area 500 may be defined for example, as a gap, an opening or a hollow in the plane under the moving web 20.

A deviation of the web in the known measurement area 500 is caused by air suction by a suction unit 900. The air suction may be provided through the known measurement area 500 or through for example, a gap or an opening below the known measurement area. The suction may be provided perpendicularly to the web 20. It may be arranged in the middle of the known measurement area.

The measurement accuracy may be enhanced when a broader area 600 is measured, slightly extended over the known measurement area 500, as illustrated in FIG. 4. The measured profile in the area 600 may thus be applied in the determination of the elastic modulus. Thus, fitting a curve to the deviation is facilitated by a rise around the known measurement area 500 and measurement accuracy may be enhanced.

In some embodiments, the measurement system or apparatus comprises means for supporting the web 20 on a surface on at least one side of the known measurement area 500. One or more supporting units may be configured support the web before and/or after the known measurement area according to the machine direction. Additionally, the web may be supported by the supporting unit at several points around the known measurement area. Having the cardboard or paper web against the measurement area and/or measurement plate and stopping or minimizing vertical movement of the moving web at the measurement point may be essential to accurate measurement, because the web may move even 120 km/h.

In the example of FIG. 4, air suction is applied by support or hold suction units 740 through holes 700 in a plane 400 arranged under a moving cardboard or paper web 20 to the said moving web for causing it against a supporting surface on both sides of the known measurement area 500. The suction for supporting the moving web and the suction causing the deviation may be provided by same or separate devices, for example, by a vacuum pump or an ejector air pump. Hence, the support units 740 may be separate units or provided by a single device providing also the suction unit 900. For example, suction levels in the range of 0-20 or 1-10 kPa may be applied for the support suction.

Figure 6:
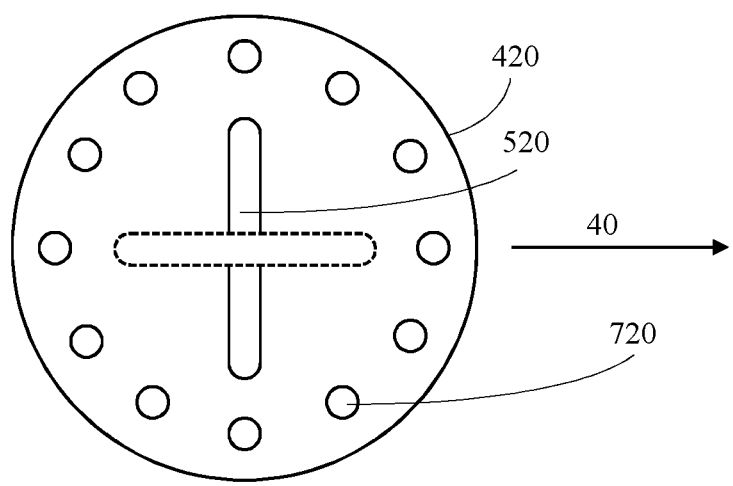
FIG. 6 illustrates a measurement plate according to one embodiment.
Figure 7:
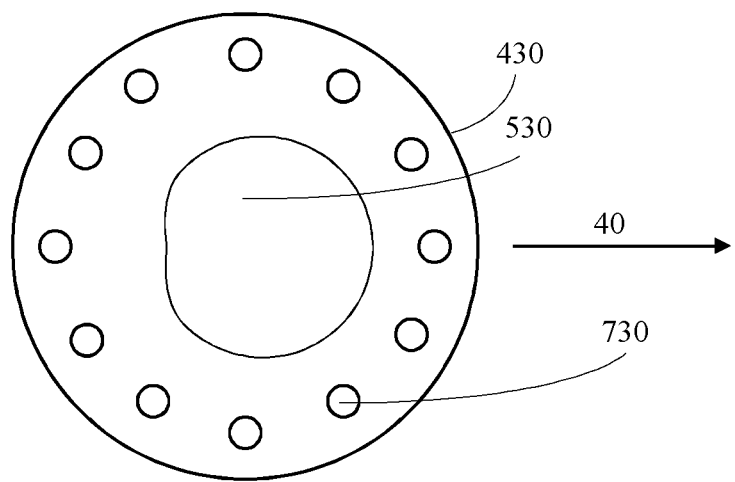
FIG. 7 illustrates a measurement plate according to one embodiment.

According to some embodiments, the apparatus comprises at least one measurement plate 410, 420, 430 to be applied against the moving cardboard or paper web 20 and comprising at least one hole 510, 520, 530 for applying suction to the moving cardboard or paper web 20. Examples of such measurement plates 410, 420, 430 are illustrated in FIGS. 5-7.

The hole 510, 520, 530 may define the known measurement area 500. The hole may be formed in the middle of the measurement plate 410, 420, 430. The shape and size of the hole may be selected according to the web properties. The shape of the hole may be for example, ellipse, circular or any other suitable form. The hole may be wider with stiffer web materials to provide sufficient deviation for measurement. The length of the hole may be for example 20-100 mm or 30-70 mm, particularly around 50 mm, and the width may be for example 2-20 mm or 5-15 mm. When comparing widths of 5 and 10 mm, the wider width enables improved detection of bending of paper web. The predetermined shape and size of the known measurement area facilitates determining and calculating of elastic modulus.

Figure 5:
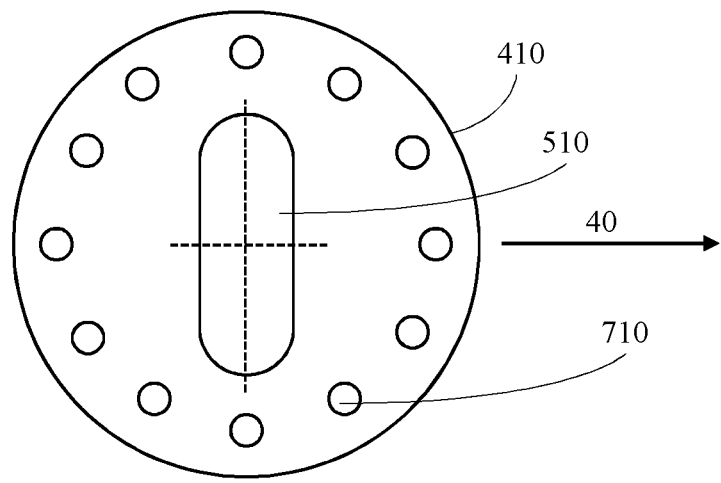
FIG. 5 illustrates a measurement plate according to one embodiment.

The longest dimension of the measurement hole 510, 520, 530 may be arranged according to the cross direction of the web 20, as shown in FIG. 5. This enables of measuring elastic modulus according to cross direction of the web. The cross directional stiffness of the packing cardboard used in cardboard boxes is usually a limiting factor during storage and transport. Thus, measuring the cross directional stiffness is useful.

According to one embodiment the measurement plate 410, 420, 430 is rotatable in relation to the moving cardboard or paper web 20. The measurement plate may be rotatable for example, at 90 degrees in relation to the moving web. It may be rotatable while moving. This enables to measure elastic modulus also according to machine direction of the web.

In addition, the measurement plate 410, 420, 430 or the measurement plate arranged in connection or in same unit with the measurement unit 30 may be arranged to move in the cross direction of the web. This enables of using several measurements points and better measurement accuracy, because the composition of the web may vary along the cross direction of the web.

The suction for supporting the web can be applied through the holes 710, 720, 730 which are circularly around the hole 510, 520, 530 defining the known measurement area on the measurement plate 410, 420, 430.

Figure 8:
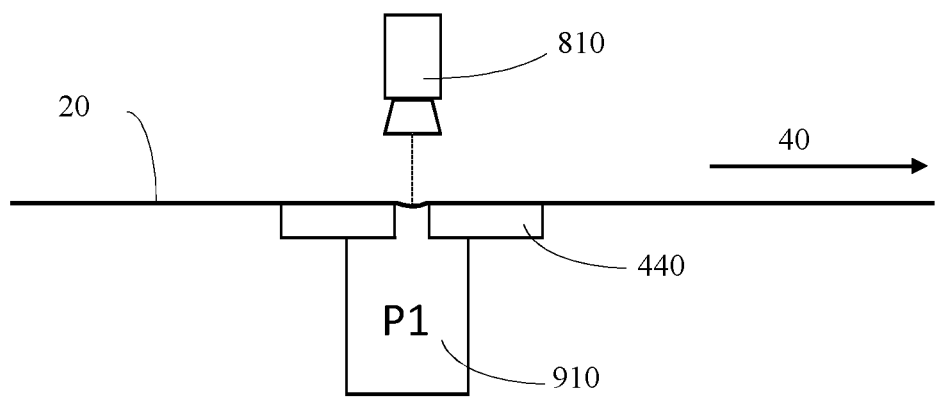
FIG. 8 illustrates two sided measurement method according to one embodiment.
Figure 9:
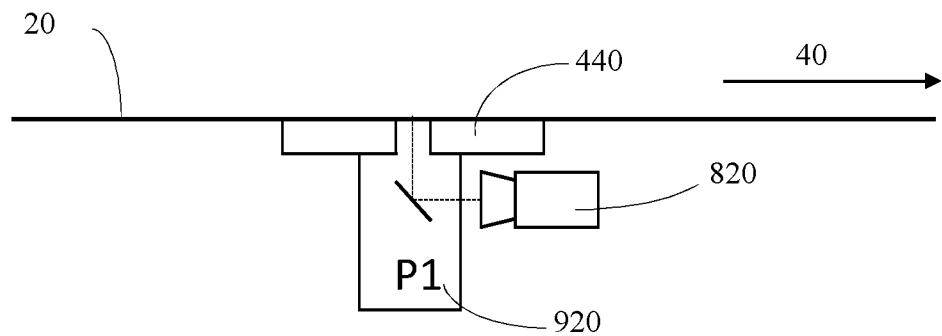
FIG. 9 illustrates one sided measurement method according to one embodiment.
Figure 10:
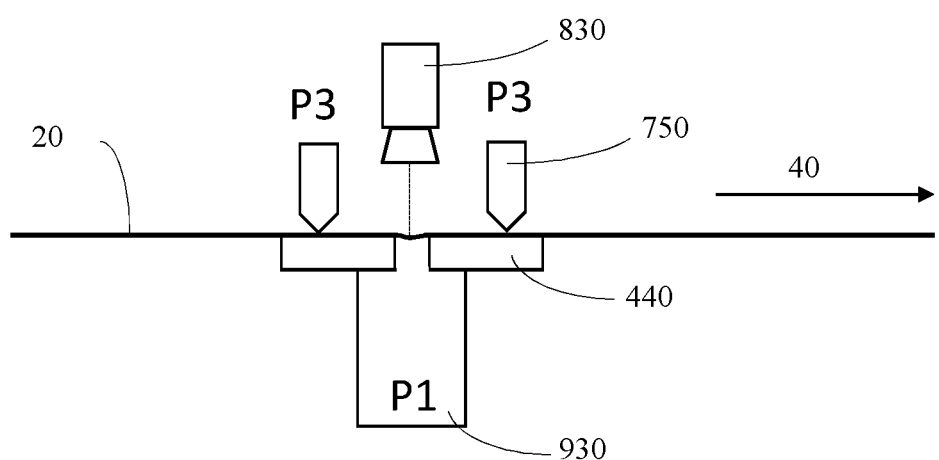
FIG. 10 illustrates measurement method with an additional supporting solution according to one embodiment.

FIGS. 8-10 illustrate some examples of different measurement arrangements. Referring to FIG. 8, a deviation sensing unit 810 and a suction unit 910 are provided at opposite sides of the moving cardboard or paper web 20. The suction unit may be placed under the web and the deviation sensing unit may be placed above the web. This measurement option is simple to implement and the measurement apparatuses require relatively little space under the web.

According to one embodiment a deviation sensing unit 820 and a suction unit 920 are provided at same side of the moving web 20, as illustrated in FIG. 9. The measurement devices for example, the deviation sensing unit and a suction unit, may be arranged in the connection or in a same measurement unit 30 on the same side of the web. For example, a lens arrangement may be applied to reorientate deviation measurement signal and facilitate sideway positioning of the deviation sensing unit. Thus, the measurement arrangement may require less space. In addition, adjustment of the measurement of the deviation to the hole 510, 520, 530 defining the known measurement area stays constant.

FIG. 10 shows measurement method with another supporting solution according to one embodiment. A mechanical web supporting unit 750 for causing a supporting force P3 to the moving web 20 against the measurement plate 440 may be placed above the web 20. The mechanical supporting force may be provided by mechanical supporting means, such as a clamp or a support rod.

A suction unit 930 is in this example placed under the web and a deviation sensing unit 830 may be placed above the web. However, it is to be appreciated that various other configurations are feasible, such as placing the suction (and possibly also the deviation sensing) above the web 20.

The apparatus for elastic modulus on-line measurement of the present invention may be placed before and/or after several different production stages in a cardboard or paper production line. This may provide a possibility to directly optimize cardboard and paper production.

According to one embodiment the apparatus is or is comprised in a paper or cardboard production machine and adapted for measuring end product of the cardboard or paper web manufacturing process. This enables of measuring the end product directly after manufacturing.

The present invention provides several advantages. It provides an apparatus by which elastic modulus of the cardboard or paper web can be measured on-line. It provides a possibility to directly optimize properties, for example stiffness, and production costs of the cardboard or paper web, because strength and elastic properties depend heavily on the amount of the raw material, treatments and additives used. The measurement unit is arranged to move in cross direction to the movement of the web, which provides using several measurements points and better measurement accuracy, because composition of the web may vary along the cross direction of the web. The measurement area is possible to define accurately by using the measurement plate with the hole defining the known measurement area. In addition, the measurement method is non-destructive, because the predetermined measurement force is caused by air.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

At least some embodiments are feasible in an on-line measurement of elastic modulus of a moving web.

ACRONYMS LIST

AI artificial intelligence
CD cross direction
MD machine direction
UI user interface

REFERENCE SIGNS LIST

10 frame
20 web
30 measurement unit
40 moving direction of web
210 causing predetermined force
220 measuring deviation
230 determining elastic modulus
301 computing unit
302 processor
303 communications unit
304 memory
305 computer program code
306 parameters
307 deviation sensing unit
308 suction unit
309 user interface
310 process automation unit(s)
311 network
400 plane arranged under web
410-440 measurement plate
500 known measurement area
510-530 hole (defining measurement area)
600 used measurement area
700-730 hole (for suction)

70 web support suction unit
750 mechanical web supporting unit
810-830 deviation sensing unit
900-930 suction unit

CITATION LIST

[1] Timoshenko, S. P., & Woinowsky-Krieger, S. (1959). Theory of Plates and Shells. McGraw-Hill.
[2] Banichuk, N., Jeronen, J., Neittaanmaki, P., Saksa, T., & Tuovinen, T. (2014). Mechanics of Moving Materials, Volume 207 of Solid Mechanics and Its Applications. Switzerland: Springer.
[3] Pratt, W. K. (2007). Digital Image Processing: PIKS Scientific Inside (Vol. 4). Hoboken, N.J.: Wiley-Inter-Science.
[4] Knowles, I., & Renka, R. J. (2014). Methods for Numerical Differentiation of Noisy Data. Electronic Journal of Differential Equations, 21(2012), 235-246.

The invention claimed is:

1. An apparatus, comprising:
a suction unit configured for applying suction with a predetermined force in a known measurement area to a moving cardboard or paper web in a manufacturing process,
a deviation sensing unit configured for on-line measurement of deviation of the moving cardboard or paper web in the manufacturing process caused by the applied suction in the known measurement area, wherein the deviation sensing unit comprises a three-dimensional scanners configured to define three-dimensional surface profile of the cardboard or paper web in the measurement area and store a set of coordinate points forming a point cloud, and
a computing unit configured for determining elastic modulus of the moving cardboard or paper web on the basis of the three-dimensional surface profile.

2. The apparatus of claim 1, wherein at least deviation sensing unit is provided in a measurement unit arranged to move in cross direction to the movement of the cardboard or paper web.

3. The apparatus of claim 1, wherein the apparatus further comprises a further suction unit for applying suction to the moving cardboard or paper web to cause the moving cardboard or paper web to move against a supporting surface of a plane of the apparatus on at least one side of the known measurement area.

4. The apparatus of claim 1, wherein the apparatus further comprises at least one measurement plate to be applied against the moving cardboard or paper web and comprising at least one hole for applying suction to the moving cardboard or paper web.

5. The apparatus of claim 4, wherein the measurement plate is rotatable in relation to the moving cardboard or paper web.

6. The apparatus of claim 1, wherein the suction unit comprises a set of selectable suction levels for applying suction to the moving cardboard or paper web.

7. The apparatus of claim 1, wherein the suction unit and the deviation sensing unit are provided at opposite sides of the moving cardboard or paper web.

8. The apparatus of claim 1, wherein the apparatus comprises a computing unit configured to determine a value indicative of strain of the moving cardboard or paper web in the direction of movement of the web, wherein the computing unit is configured to calculate the elastic modulus on the basis of the determined value indicative of the strain.

9. The apparatus of claim 1, wherein the apparatus is a paper or cardboard production machine or is to be included in a paper or cardboard production machine, wherein the apparatus is adapted for measuring end product properties in the cardboard or paper web manufacturing process.

10. The apparatus of claim 1, wherein the apparatus is configured to measure an area which extends outside said known measurement area.

11. A method for measurement of elastic modulus of a moving cardboard or paper web, comprising:
controlling suction with predetermined force in a known measurement area to a moving cardboard or paper web in a manufacturing process,
detecting on-line measurement information on deviation of the moving cardboard or paper web in the manufacturing process caused by the suction with predetermined force in the known measurement area, wherein a three-dimensional surface profile of the cardboard or paper web in the measurement area is provided and a set of coordinate points forming a point cloud is stored, and
determining elastic modulus of the moving cardboard or paper web in the manufacturing process on the basis of the three-dimensional surface profile.

12. The method of claim 11, wherein suction is applied to the moving cardboard or paper web for causing the moving cardboard or paper web against a surface on at least one side of the known measurement area.

13. The method of claim 11, wherein an area which extends outside said known measurement area is measured.

14. A non-transitory computer readable medium, comprising computer program code for, when executed in a processor of a computing device for an elastic modulus measurement system, causing the computing device at least to:
control suction by a suction unit with predetermined force in a known measurement area to a moving cardboard or paper web in a manufacturing process,
detect from a deviation sensing unit on-line measurement information on the deviation of the moving cardboard or paper web in the manufacturing process caused by the suction with predetermined force in the known measurement area, wherein a three-dimensional profile of the cardboard or paper web in the measurement area is provided and a set of coordinate points forming a point cloud is stored, and
determine elastic modulus of the moving cardboard or paper web in the manufacturing process on the basis of the three-dimensional surface profile.

* * * * *